United States Patent
Godwin et al.

(10) Patent No.: US 9,415,115 B2
(45) Date of Patent: Aug. 16, 2016

(54) CONJUGATED PROTEINS AND PEPTIDES

(71) Applicant: POLYTHERICS LIMITED, Cambridge (GB)

(72) Inventors: Antony Robert Godwin, London (GB); Stephen James Brocchini, Welwyn Garden (GB)

(73) Assignee: POLYTHERICS LIMITED, Cambridge (GB)

( * ) Notice: Subject to any disclaimer, the term of this patent is extended or adjusted under 35 U.S.C. 154(b) by 0 days.

(21) Appl. No.: 14/659,598

(22) Filed: Mar. 16, 2015

(65) Prior Publication Data
US 2015/0216994 A1 Aug. 6, 2015

Related U.S. Application Data

(62) Division of application No. 13/254,003, filed as application No. PCT/GB2010/000393 on Mar. 4, 2010, now Pat. No. 9,005,598.

(30) Foreign Application Priority Data

| Mar. 4, 2009 | (GB) | .................................. 0903746.6 |
| Jul. 17, 2009 | (GB) | .................................. 0912485.0 |
| Dec. 21, 2009 | (GB) | .................................. 0922354.6 |

(51) Int. Cl.
| C07K 1/00 | (2006.01) |
| A61K 47/48 | (2006.01) |
| A61K 38/21 | (2006.01) |
| A61K 39/395 | (2006.01) |

(52) U.S. Cl.
CPC ......... *A61K 47/48215* (2013.01); *A61K 38/212* (2013.01); *A61K 39/395* (2013.01)

(58) Field of Classification Search
CPC ........... A61K 47/48215; A61K 38/212; A61K 39/395
USPC .............................................. 530/351, 391.1
See application file for complete search history.

(56) References Cited

U.S. PATENT DOCUMENTS

| 5,446,090 | A | 8/1995 | Harris |
| 5,739,208 | A | 4/1998 | Harris |
| 6,362,254 | B2 | 3/2002 | Harris et al. |
| 6,664,331 | B2 | 12/2003 | Harris et al. |
| 6,908,963 | B2 | 6/2005 | Roberts et al. |
| 7,030,278 | B2 | 4/2006 | Harris et al. |
| 7,078,496 | B2 | 7/2006 | Roberts et al. |
| 7,223,803 | B2 | 5/2007 | Harris et al. |
| 7,511,095 | B2 | 3/2009 | Roberts et al. |
| 7,528,202 | B2 | 5/2009 | Harris et al. |
| 7,595,292 | B2 | 9/2009 | Brocchini et al. |
| 7,714,088 | B2 | 5/2010 | Harris et al. |
| 7,834,088 | B2 | 11/2010 | Roberts et al. |
| 7,939,630 | B2 | 5/2011 | Brocchini et al. |
| 8,003,742 | B2 | 8/2011 | Harris et al. |
| 8,618,333 | B2 | 12/2013 | Godwin |
| 8,816,051 | B2 | 8/2014 | Brocchini et al. |
| 2003/0105224 | A1 | 6/2003 | Roberts et al. |
| 2003/0158333 | A1 | 8/2003 | Roberts et al. |
| 2004/0059025 | A1 | 3/2004 | Harris et al. |
| 2006/0178505 | A1 | 8/2006 | Roberts et al. |
| 2006/0210526 | A1 | 9/2006 | Brocchini et al. |
| 2009/0298154 | A1 | 12/2009 | Brocchini et al. |
| 2010/0069571 | A1 | 3/2010 | Roberts et al. |
| 2010/0239517 | A1 | 9/2010 | Brocchini et al. |
| 2011/0065862 | A1 | 3/2011 | Roberts et al. |
| 2011/0136723 | A1 | 6/2011 | Godwin |
| 2011/0182855 | A1 | 7/2011 | Brocchini et al. |
| 2011/0262994 | A1 | 10/2011 | Godwin |
| 2012/0014905 | A1 | 1/2012 | Godwin et al. |
| 2012/0115772 | A1 | 5/2012 | Choi et al. |
| 2013/0338231 | A1 | 12/2013 | Godwin et al. |
| 2014/0081047 | A1 | 3/2014 | Godwin |
| 2014/0369960 | A1 | 12/2014 | Brocchini et al. |

FOREIGN PATENT DOCUMENTS

| WO | 2005/007197 | 1/2005 |
| WO | 2008/098930 | 8/2008 |
| WO | 2009/047500 | 4/2009 |

OTHER PUBLICATIONS

Blasovich & Kahn "Polymer-supported acetylide addition to hexa-2,4-dienal" *Synthesis*, vol. 1998, No. 7, pp. 965-966 (Jul. 1998).
Brocchini et al. "Disulfide bridge based PEGylation of proteins" *Advanced Drug Delivery Reviews*, vol. 60, No. 1, pp. 3-12 (Jan. 2008).
Int'l Search Report for PCT/GB2010/000393, four pages, mailed Aug. 20, 2010.
Written Opinion for PCT/GB2010/000393, seven pages, dated Aug. 20, 2010.
European Patent Office examination report for related application EP 10707337.1, six pages, dated Jan. 8, 2013.
Delattre et al. "1,3-Dipolar cycloaddition reaction of bipyridinium ylides with the propynamido-β-cyclodextrin. A regiospecific synthesis of a new class of fluorescent β-cyclodextrins" *Tetrahedron*, vol. 60, No. 7, pp. 1557-1562 (Feb. 2004).

*Primary Examiner* — Jason Sims
*Assistant Examiner* — Ibrahim D Bori
(74) *Attorney, Agent, or Firm* — Nixon & Vanderhye PC

(57) ABSTRACT

Novel compounds of the general formula:

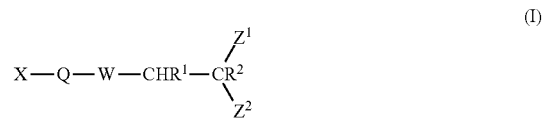

(I)

in which X represents a polymer,
Q represents a linking group;
W represents an electron-withdrawing moiety or a moiety preparable by reduction of an electron-withdrawing moiety; each of $R^1$ and $R^2$ independently represents a hydrogen atom or a $C_{1-4}$ alkyl group; and
either $Z^1$ represents a protein or a peptide linked to $CR^2$ via a nucleophilic moiety, and $Z^2$ represents a molecule linked to $CR^2$ via a nucleophilic moiety, or $Z^1$ and $Z^2$ together represent a single group derived from a protein or peptide linked to $CR^2$ via two nucleophilic moieties.

12 Claims, 5 Drawing Sheets

CONJUGATED PROTEINS AND PEPTIDES

This application is a division of application Ser. No. 13/254,003, filed Sep. 29, 2011, now U.S. Pat. No. 9,005,598; which is the U.S. national stage under 35 U.S.C. 371 of Application No. PCT/GB2010/000393, filed Mar. 4, 2010, which claimed priority benefit of Application Nos. GB 0903746.6, filed Mar. 4, 2009; GB 0912485.0, filed Jul. 17, 2009; and GB 0922354.6, filed Dec. 21, 2009; the entire contents of each of which are hereby incorporated by reference.

This invention relates to novel conjugated proteins and peptides, and their preparation.

Many therapeutically active molecules, for example proteins, do not possess the properties required to achieve efficacy in clinical medical use. For example, many native proteins do not make good medicines because upon administration to patients there are several inherent drawbacks that include: (1) proteins are digested by many endo- and exo-peptidases present in blood or tissue; (2) many proteins are immunogenic to some extent; and (3) proteins can be rapidly excreted by kidney ultrafiltration and by endocytosis. Some molecules which might find utility as active therapeutic agents in medicines are systemically toxic or lack optimal bioavailability and pharmacokinetics. When proteins clear from the blood circulation quickly they typically have to be administered to the patient frequently. Frequent administration further increases the risk of toxicity, especially immunologically derived toxicities.

Water soluble, synthetic polymers, particularly polyalkylene glycols, are widely used to conjugate therapeutically active molecules such as proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation".

It is important for optimised efficacy and to ensure dose to dose consistency that the number of conjugated polymer molecules per protein is the same for each molecule, and that each polymer molecule is specifically covalently conjugated to the same amino acid residue in each protein molecule. Non-specific conjugation at sites along a protein molecule results in a distribution of conjugation products and, frequently, unconjugated protein, to give a complex mixture that is difficult and expensive to purify.

WO 2005/007197 describes a series of novel conjugation reagents which can be used to react with nucleophilic groups in a biological molecule, for example a protein, to produce a protein-polymer conjugate. These reagents find particular utility for their ability to conjugate with both sulfur atoms derived from a disulfide bond in a protein to give novel thioether conjugates. The reagents of WO 2005/007197 result in products having at least 3 carbon atoms between the cross-linked nucleophilic groups, typically sulfur atoms, linking the protein(s).

We have now found a novel series of protein conjugation reagents which can be used to conjugate to two nucleophilic groups, resulting in a product with only a single carbon atom between those groups.

Accordingly, the present invention provides a compound of the general formula:

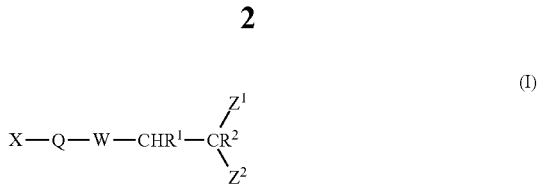

(I)

in which X represents a polymer;
Q represents a linking group;
W represents an electron-withdrawing moiety or a moiety preparable by reduction of an electron-withdrawing moiety;
each of $R^1$ and $R^2$ independently represents a hydrogen atom or a $C_{1-4}$alkyl group; and
either $Z^1$ represents a protein or a peptide linked to $CR^2$ via a nucleophilic moiety, and $Z^2$ represents a molecule linked to $CR^2$ via a nucleophilic moiety, or $Z^1$ and $Z^2$ together represent a single group derived from a protein or peptide linked to $CR^2$ via two nucleophilic moieties.

Throughout this specification, the term "protein" will on occasions be used for convenience, and except where the context requires otherwise, references to "protein" should be understood to be references to "protein or peptide". $Z^1$ in the novel conjugate of the present invention is derived from a protein. $Z^2$ may also be derived from a protein (in which case $Z^2$ may represent the same protein as $Z^1$ or a different protein), but may also be derived from any other desired molecule containing a nucleophilic group. $Z^1$ and $Z^2$ together may represent a single group derived from a protein.

Further, a protein from which $Z^1$ and/or $Z^2$ is derived may be derivatised or functionalised if desired. In particular, prior to conjugation, a native protein may have been reacted with various blocking groups to protect sensitive groups thereon; or it may have been previously conjugated with one or more polymers, either using the process of this invention or using an alternative process. As well as or instead of being previously conjugated to one or more polymers, the protein may have been conjugated to one or more molecules selected, for example, from other proteins; small molecules, for example therapeutics or diagnostics; sialic acid; sugars; and starches.

A polymer X may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally X may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer X may be a homopolymer, random copolymer or a structurally defined copolymer such as a block copolymer, for example X may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid) and derivatives thereof. A protein may be used as the polymer. This allows conjugation of one protein, for example an antibody or antibody fragment, to a second protein, for example an enzyme or other active protein. Also, if a peptide containing a catalytic sequence is used, for example an O-glycan acceptor site for glycosyltransferase, it allows the incorporation of a substrate or a target for subsequent enzymatic reaction. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted polyalkylene glycols, for example methoxypolyethylene glycol, may be used. In a preferred embodiment of the invention, a single-chain polyethylene glycol is initiated by a suitable group, for example an alkoxy, e.g. methoxy, aryloxy, carboxy or hydroxyl group, and is connected at the other end of the chain to the linker group Q.

The polymer X may optionally be derivatised or functionalised in any desired way. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. Multimeric conjugates that contain more than one biological molecule, can result in synergistic and additive benefits. If desired, the polymer may be coupled to a solid support using conventional methods.

The optimum molecular weight of the polymer will of course depend upon the intended application. Preferably, the number average molecular weight is in the range of from 500 g/mole to around 75,000 g/mole. When the compound of the general formula I is intended to leave the circulation and penetrate tissue, for example for use in the treatment of inflammation caused by malignancy, infection or autoimmune disease, or by trauma, it may be advantageous to use a lower molecular weight polymer in the range 2000-30,000 g/mole. For applications where the compound of the general formula I is intended to remain in circulation it may be advantageous to use a higher molecular weight polymer, for example in the range of 20,000-75,000 g/mole.

The polymer to be used should be selected so the conjugate is soluble in the solvent medium for its intended use. For biological applications, particularly for diagnostic applications and therapeutic applications for clinical therapeutic administration to a mammal, the conjugate will be soluble in aqueous media. Many proteins such as enzymes have utility in industry, for example to catalyze chemical reactions. For conjugates intended for use in such applications, it may be necessary that the conjugate be soluble in either or both aqueous and organic media. The polymer should of course not unduly impair the intended function of the protein.

Preferably the polymer is a synthetic polymer, and preferably it is a water-soluble polymer. The use of a water-soluble polyethylene glycol is particularly preferred for many applications.

Linking group Q may for example be a direct bond, an alkylene group (preferably a $C_{1-10}$ alkylene group), or an optionally-substituted aryl or heteroaryl group, any of which may be terminated or interrupted by one or more oxygen atoms, sulphur atoms, —NR groups (in which R has the meaning given below), keto groups, —O—CO— groups and/or —CO—O— groups. Suitable aryl groups include phenyl and naphthyl groups, while suitable heteroaryl groups include pyridine, pyrrole, furan, pyran, imidazole, pyrazole, oxazole, pyridazine, primidine and purine. The linkage to the polymer X may be by way of a hydrolytically labile bond, or by a non-labile bond.

Substituents which may be present on an optionally substituted aryl or heteroaryl group include for example one or more of the same or different substituents selected from —CN, —NO$_2$, —CO$_2$R, —COH, —CH$_2$OH, —COR, —OR, —OCOR, —OCO$_2$R, —SR, —SOR, —SO$_2$R, —NHCOR, —NRCOR, —NHCO$_2$R, —NR'CO$_2$R, —NO, —NHOH, —NR'OH, —C=N—NHCOR, —C=N—NR'COR, —N$^+$R$_3$, —N$^+$H$_3$, —N$^+$HR$_2$, —N$^+$H$_2$R, halogen, for example fluorine or chlorine, —C≡CR, —C=CR$_2$ and —C=CHR, in which each R or R' independently represents a hydrogen atom or an alkyl (preferably $C_{1-6}$ alkyl) or an aryl (preferably phenyl) group. The presence of electron withdrawing substituents is especially preferred.

W may for example represent a keto group CO, an ester group —O—CO—, an amide group —NH—CO—, or a sulfone group —SO$_2$—, or a group obtained by reduction of such a group, e.g. a CH.OH group, an ether group CH.OR, an ester group CH.O.C(O)R, an amine group CH.NH$_2$, CH.NHR or CH.NR$_2$, or an amide CH.NHC(O)R or CH.N(C(O)R)$_2$.

The present invention allows the conjugation of a polymer to a group $Z^1$ which is a protein, and to a second group $Z^2$ which may also be derived from a protein, either the same or different from $Z^1$, but which may also be derived from any other desired molecule containing a nucleophilic group. For example, $Z^2$ may be a chelating agent which could then be used to chelate any other desired moiety, for example a radio nucleotide; a fluorescent agent, for example an amine derivatised fluorescent probe such as 5-dimethylaminonaphthalene-1-(N-(2 aminoethyl))sulfonamidedansyl ethylenediamine, OREGON GREEN® 488 cadaverine (catalogue number 0-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L-2424, Molecular Probes), or a thiol derivatised fluorescent probe for example BODIPY® FL L-cystine (catalogue number B-20340, Molecular Probes); or a drug molecule.

In the following portion of this specification, unless the context requires otherwise, $Z^1$ and $Z^2$ will be referred to collectively as Z. It is a preferred embodiment of the invention that $Z^1$ and $Z^2$ together should represent a single protein, in which case the compound of the invention has the general formula:

(Ia)

Preferably a nucleophilic moiety linking $CR^2$ to the group(s) Z is derived from a thiol group or an amine group. Two thiol groups may be generated by reduction of a natural or engineered disulfide (cysteine) bridge. Amine groups may for example be lysine or histidine residues. Where $Z^1$ and $Z^2$ together form a single protein which is linked to $CR^2$ via two thiol groups, the compound of the formula I has the formula:

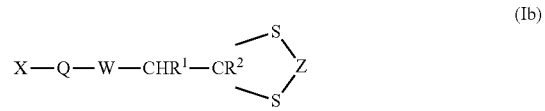
(Ib)

Such conjugates form a preferred embodiment of the invention.

In a further preferred embodiment of the invention, a single protein may be linked to $CR^2$ via two histidine residues. These two residues may be present in the native protein, and if so, the two residues must be located sufficiently close together in the native structure to enable conjugation to $CR^2$. This may occur when two histidine residues are adjacent to each other in the protein chain, or they may be close together as a result of the folding of the protein. Such proteins generally bind to IMAC columns. For example, the prokaryotic organism *Escherichia coli* has one protein known as YODA where binding to IMAC columns can occur. Preferably, however, the two histidine residues form part of a polyhistidine tag, i.e. a histidine chain, not found in the native protein, which has been attached to the protein by suitable means, for example by chemical means, by post-translational labelling with a polyhistidine tag or a moiety containing a polyhistidine tag, or via protein engineering by inserting histidine sequences in fusion with the target protein, for example by the use of a gene having a short coding sequence which codes for a polyhistidine tag of the desired length.

Polyhistidine tags may contain any desired number of histidine residues, for example up to about 12 residues. They must contain at least 2 residues; preferably they contain at least 3 residues, especially from 4 to 10 residues, especially from 5 to 8 residues, for example 5 or 6 residues. They may contain only histidine residues, or they may also contain one or more spacer residues or sequences in addition to histidine residues. Bonding to a polyhistidine tag is likely to be to adjacent histidine residues, but bonding to spaced apart histidine residues, providing that the spacing is not too large to prevent formation of the conjugate, cannot be ruled out.

Many proteins supplied commercially contain polyhistidine tags, either because the protein has been previously purified by way of IMAC, or to aid future purification of the protein itself or products derived from it. If it is desired to conjugate the protein to a polymer, conjugation to the polyhistidine tag provides an extremely convenient route, previously not envisaged. Conjugated products, specifically PEGylated products, can be obtained with a high degree of consistency. Use of the conjugating reagents of the present invention, resulting in conjugation to two histidine residues, results in a macrocycle, leading to a particularly stable and selective conjugate, generally obtained in high yield.

Because the polyhistidine tag is generally attached to the surface of the protein, generally at one end of the protein chain, and can be positioned at any desired site in the protein, the biological activity of the protein is largely maintained following the process for introducing a polyhistidine tag, and also following the subsequent process of site-specific conjugation at the polyhistidine tag to a polymer. For these reasons, the present invention can be used to form conjugates of proteins which have previously proved intractable to traditional conjugation processes.

Provided that a polyhistidine tag contains a sufficient number of histidine residues, a conjugate of the present invention may still be purified using IMAC. For this to be effective, at least two, preferably more, histidine residues in the polyhistidine tag need to remain unconjugated and available for binding to the nickel in the IMAC column. The reduction in the number of free histidine residues post conjugation allows for selectivity in binding to the IMAC column between unconjugated peptide or protein and the conjugated derivative. Where multiple conjugation occurs to the same biological molecule, IMAC allows for separation of the multi-conjugated derivatives.

The invention also provides a process for the preparation of a compound of the general formula I, which comprises reacting a compound of the general formula $$X\text{-}Q\text{-}W'\text{-}CR^1R^{1'}\text{—}CR^2.L.L' \quad (II)$$

in which X represents a polymer;
Q represents a linking group;
W' represents an electron-withdrawing group;
either $R^1$ represents a hydrogen atom or a $C_{1-4}$ alkyl group, $R^{1'}$ represents a hydrogen atom, and each of L and L' independently represents a leaving group; or
$R^1$ represents a hydrogen atom or a $C_{1-4}$ alkyl group, L represents a leaving group, and $R^{1'}$ and L' together represent a bond; or $R^1$ and L together represent a bond and $R^{1'}$ and L' together represent a bond; and
$R^2$ represents a hydrogen atom or a $C_{1-4}$ alkyl group;
with a protein or a peptide containing at least one nucleophilic group, and optionally subsequently with a second molecule containing a nucleophilic group.

The compounds of the general formula II are novel, and the invention therefore provides these compounds per se.

When the compound of the formula II has the formula IIa:

$$X\text{-}Q\text{-}W'\text{-}CR^1R^{1'}\text{—}CR^2.L.L' \quad (IIa)$$

in which $R^1$ represents a hydrogen atom or a $C_{1-4}$ alkyl group, $R^{1'}$ represents a hydrogen atom, and each of L and L' independently represents a leaving group, two leaving groups are present.

When the compound of the formula II has the formula IIb:

$$X\text{-}Q\text{-}W'\text{-}CR^1\text{=}CR^2\text{-}L \quad (IIb)$$

in which $R^1$ represents a hydrogen atom or a $C_{1-4}$ alkyl group, and L represents a leaving group, only one leaving group is present.

When the compound of formula II has the formula IIc:

$$X\text{-}Q\text{-}W'\text{-}C\text{≡}CR^2 \quad IIc$$

no leaving groups are present, and $R^1$ in the resulting compound of the general formula I is a hydrogen atom.

The compounds of formula IIa, IIb and IIc are chemically equivalent to each other. Under suitable reaction conditions, a compound of formula IIa is converted in situ into a compound of formula IIb, which in turn, if $R^1$ is a hydrogen atom, may be converted in situ into a compound of formula IIc.

If present, a leaving group L or L' in formula II may for example represent —SR, —$SO_2R$, —$OSO_2R$, —$N^+R_3$, —$N^+HR_2$, —$N^+H_2R$, halogen, or —OØ, in which R has the meaning given above, and Ø represents a substituted aryl, especially phenyl, group, containing at least one electron withdrawing substituent, for example —CN, —$NO_2$, —$CO_2R$, —COH, —$CH_2OH$, —COR, —OR, —OCOR, —$OCO_2R$, —SR, —SOR, —$SO_2R$, —NHCOR, —NRCOR, —$NHCO_2R$, —$NR'CO_2R$, —NO, —NHOH, —NR'OH, —C≡N—NHCOR, —C≡N—NR'COR, —$N^+R_3$, —$N^+HR_2$, —$N^+H_2R$, halogen, especially chlorine or, especially, fluorine, —C≡CR, —C≡$CR_2$ and —C≡CHR, in which R and R' have the meanings given above. If two leaving groups L and L' are present, these may be the same or different, but are preferably the same.

An electron withdrawing group W may for example be a keto group, an ester group —O—CO—, an amide group —NH—CO—, or a sulfone group —$SO_2$—.

The process may be carried out in a solvent or solvent mixture in which all reactants are soluble. Advantageously, an aqueous reaction medium is used. This reaction medium may also be buffered, depending on the pH requirements of the nucleophile. The optimum pH for the reaction will generally be between pH 3.5 and pH 8.5, for example between pH 5.5 and pH 8.5.

Reaction temperatures between 3-37° C. are generally suitable: proteins may decompose or denature impairing function if the conjugation reaction is conducted at a temperature where these processes may occur. Reactions conducted in organic media (for example THF, ethyl acetate, acetone) are typically conducted at temperatures up to ambient.

The immediate product of the process according to the invention is a compound of the general formula I in which W is an electron-withdrawing group. Because the process of the invention is reversible under suitable conditions, such compounds have utility in themselves, for example when release of the free protein is required, for example in direct clinical applications. An electron-withdrawing moiety W may, however, be reduced. The resulting moiety gives a moiety which prevents release of the protein, and such compounds will also have utility in many clinical, industrial and diagnostic applications.

Thus, for example, a moiety W' containing a keto group may be reduced to a moiety W containing a CH(OH) group; an ether group CH.OR may be obtained by the reaction of a hydroxy group with an etherifying agent; an ester group CH.O.C(O)R may be obtained by the reaction of a hydroxy group with an acylating agent; an amine group CH.NH$_2$, CH.NHR or CH.NR$_2$ may be prepared from a ketone or aldehyde by reductive amination); or an amide CH.NHC(O)R or CH.N(C(O)R)$_2$ may be formed by acylation of an amine).

The compounds of the general formula I have a number of applications. They may for example be used for direct clinical application to a patient, and accordingly, the present invention further provides a pharmaceutical composition comprising a compound of the general formula I together with a pharmaceutically acceptable carrier. The invention further provides a compound of the general formula I for use in therapy, and a method of treating a patient which comprises administering a pharmaceutically effective amount of a compound of the formula I or a pharmaceutical composition according to the invention to the patient. Any desired pharmaceutical effect, for example trauma treatment, enzyme replacement, protein replacement, wound management, toxin removal, anti-inflammatory, anti-infective, immunomodulatory, vaccination or anti-cancer, may be obtained by suitable choice of protein.

The compounds of the general formula I may also be used in non-clinical applications. For example, many physiologically active compounds such as enzymes are able to catalyse reactions in organic solvents, and compounds of the general formula I may be used in such applications. Further, compounds of the general formula I may be used as diagnostic tools.

Compounds of the general formula I may include an imaging agent, for example a radio nucleotide, to enable tracking of the compound in vivo.

A protein present in the conjugate of the invention may for example be a peptide, polypeptide, antibody, antibody fragment, enzyme, cytokine, chemokine, receptor, blood factor, peptide hormone, toxin, transcription protein, or multimeric protein. Constrained or cyclic polypeptides, which are usually cyclised through a disulfide bridge, and epitopes, may be used. The following gives some specific proteins which may have utility in the present invention, depending upon the desired application.

Enzymes include carbohydrate-specific enzymes, proteolytic enzymes and the like. Enzymes of interest, for both industrial (organic based reactions) and biological applications in general and therapeutic applications in particular include the oxidoreductases, transferases, hydrolases, lyases, isomerases and ligases disclosed by U.S. Pat. No. 4,179,337.

Specific enzymes of interest include asparaginase, arginase, adenosine deaminase, superoxide dismutase, catalase, chymotrypsin, lipase, uricase, bilirubin osidase, glucose oxidase, glucuronidase, galactosidase, glucocerbrosidase, glucuronidase, glutaminase The proteins used in compounds of the general formula I of the present invention include for example factor 8, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, colony stimulating factors, hemoglobin, cytokines, antibodies, chorionicgonadotropin, follicle-stimulating hormone, thyroid stimulating hormone and tissue plasminogen activator.

Certain of the above proteins such as the interleukins, interferons and colony stimulating factors also exist in non-glycosilated form, usually the result of preparation by recombinant protein techniques. The non-glycosylated versions may be used in the present invention.

Other proteins of interest are allergen proteins disclosed by Dreborg et al. Crit. Rev. Therap. Drug Carrier Syst. (1990) δ: 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosilated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes. The antibody may used alone or may be covalently conjugated ("loaded") with another atom or molecule such as a radioisotope or a cytotoxic/antiinfective drug. Epitopes may be used for vaccination to produce an immunogenic polymer-protein conjugate.

The following Examples illustrate the invention.

EXAMPLE 1

Figure 1:
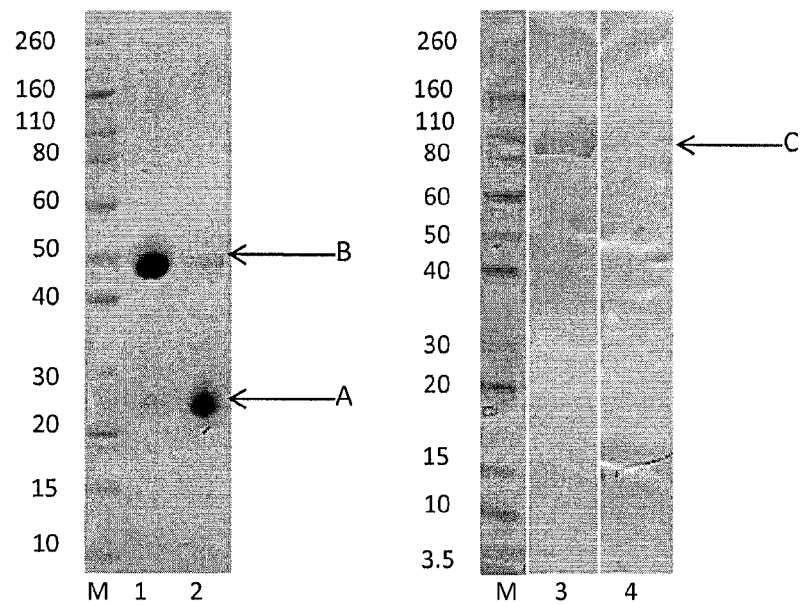
FIG. 1 shows the results of Example 3.

Synthesis of 20 kDa PEG Reagent 1

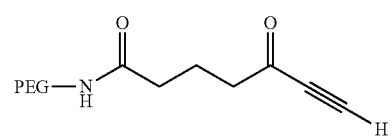

Step 1. Deprotection of 5-oxo-7-(trimethylsilyl)hept-6-ynoic acid

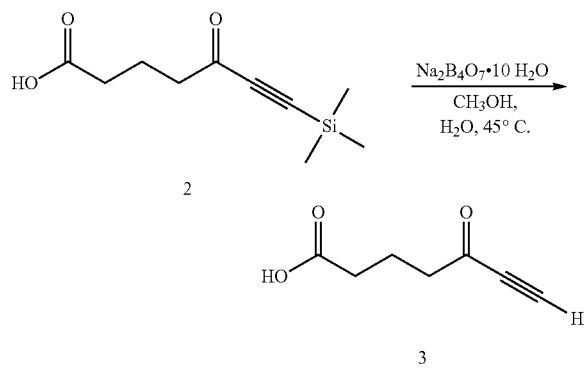

The known 5-oxo-7-(trimethylsilyl)hept-6-ynoic acid (1.15 g, 2; prepared using the procedure described in J. Org. Chem., Vol. 62, No. 4, 1997, pp. 982-991) was dissolved in methanol (40 ml) and a solution of Borax ($Na_2B_4O_7 \times 10H_2O$, 2.7 g) in water (6 ml) was added. The resulting reaction mixture was stirred for 18 h at 45° C. under argon. The reaction mixture was then quenched by the addition of 1 M HCl (20 ml) and methanol removed in vacuo. The remaining aqueous solution was then extracted with ethyl acetate (4×35 ml). After washing the pooled organic extracts with brine (2×40 ml), drying with $MgSO_4$ and then filtering, volatiles were removed in vacuo. The crude orange oil remaining was purified by flash chromatography (5% ethyl acetate→10%→15% ethyl acetate/hexane) yielding a pale yellow oil product, 5-oxohept-6-ynoic acid (328 mg, J), which crystallized under storage. $^1$H NMR (400 MHz, $CDCl_3$): δ1.75 (m, 2H), 2.22 (t, 2H), 2.63 (t, 2H), 4.8 (s, 1H).

Step 2. Conjugation of 5-oxohept-6-ynoic acid 3 with 20 kDa PEG to give PEG reagent 1

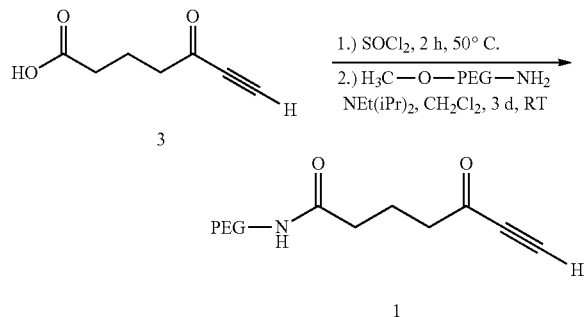

A one-neck 50 ml schlenk flask was charged with the 5-oxohept-6-ynoic acid (28 mg, 3) and a magnetic stir bar. The neck part of the flask was sealed with a septum and the flask placed under strong vacuum using an oil pump for approximately 15 min. An argon atmosphere was introduced into the flask by placing an argon filled balloon fitted with a needle through the septum. Thionyl chloride ($SOCl_2$, 1 mL) was then injected into the flask with stirring and the resulting mixture was heated at 50° C. for 1.5 h. Volatiles where then removed using an oil pump to afford a yellow-brown oil. An argon atmosphere was again introduced by balloon and anhydrous dichloromethane (5 ml) was added by syringe to afford a homogeneous solution again. Volatiles were then removed using an oil pump. The solvent addition/removal process was repeated once more. Anhydrous dichloromethane (5 mL) was again added to the schlenk flask to form a homogeneous solution. Separately in a 25 ml round bottom flask fitted with a septum and with a magnetic stir bar, O-(2-aminoethyl)-O'-methylpolyethylene glycol (200 mg, 20 kDa) and anhydrous ethyldiisopropylamine (35 μL) were dissolved in anhydrous dichloromethane (5 ml) under an argon atmosphere. Using a syringe and argon filled balloon to equalise the pressure, the thionyl chloride activated solution of was injected into the flask containing the PEG solution in a dropwise fashion, immediately resulting in the evolution of a white gas. The resulting solution was allowed to stir over the weekend (3 days) at room temperature. Volatiles were removed under vacuum (30° C., water bath) and the solid residue obtained was redissolved with gentle heating (35° C.) in acetone (12 mL) and filtered over non-absorbent cotton wool. The solution was then cooled in a dry ice bath to give a white precipitate that was separated by centrifugation (−9° C., 4600 rpm, 15 min, swinging bucket rotor) followed by decantation. The precipitation procedure was repeated four times. Afterward the resulting PEG reagent 1 was allowed to dry under vacuum (189 mg). Conjugation of 3 to the PEG-amine was confirmed by the disappearance of the NMR signal for the methylene group immediately adjacent to the amine group of the starting PEG at approximately 2.9 ppm in the NMR spectrum (DMSO-$d_6$) of product 1.

EXAMPLE 2

Synthesis of 10 kDa PEG Reagent 6

Step 1:

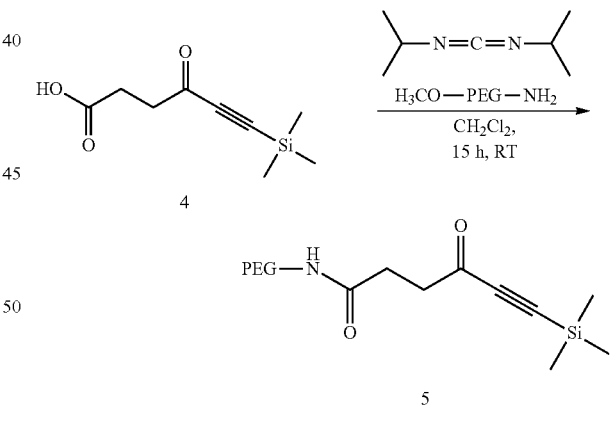

O-(2-aminoethyl)-O'-methyl-PEG (MW 10 kDa, 200 mg, dried from toluene solution) and 4-oxo-6-(trimethylsilyl)hex-5-ynoic acid (20 mg, 4; prepared using the procedure described in J. Org. Chem., Vol. 62, No. 4, 1997, pp. 982-991) was dissolved in dry dichloromethane (10 mL) under argon. To the resulting solution was added diisopropylcarbodiimide (DIPC, 17 μL). The reaction mixture was allowed to stir at room temperature over night (15 h). Volatiles were removed under vacuum (30° C., water bath) and the solid residue obtained was redissolved with gentle heating (35° C.) in acetone (12 mL) and filtered over non-absorbent cotton wool to remove the insoluble material. The solution was then cooled in a dry ice bath to give a white precipitate that was separated by centrifugation (−9° C., 4600 rpm, 15 min, swinging bucket rotor) followed by decantation.

The precipitation procedure was repeated four times. The resulting solid 5 was allowed to dry under vacuum (193 mg). The identity of the product was confirmed by the presence of diagnostic signals for the silyl methyls at 0.2 ppm, non-PEG methylene groups at 2.49 and 2.96 ppm, and the methoxy group of PEG at 3.38 ppm in the NMR spectrum of product 5 performed in $CDCl_3$ (400 MHz).

Step 2. Deprotection of the PEGylated trimethylsilyl acetylenic keto acid 5 to give the PEG reagent 6

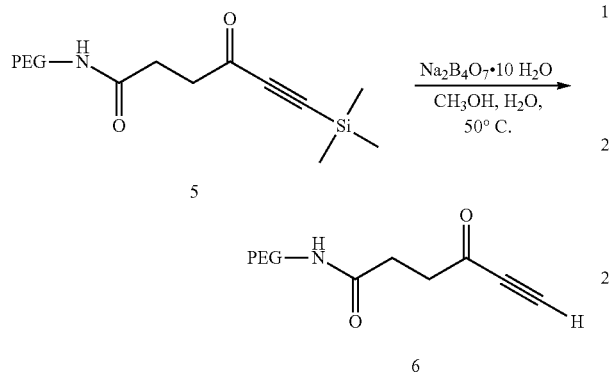

The PEGylated trimethylsilyl acetylenic keto acid (100 mg, 5) was dissolved in methanol (4 mL), then a solution of Borax ($Na_2B_4O_7 \times 10H_2O$, 5 mg) in water (0.6 mL) was added and the reaction mixture was stirred for 18 h at 50° C. under argon. The reaction mixture was then quenched by the addition of 1 M HCl (1 mL) and the solvents removed in vacuo at 30° C. affording a brown solid. The residue was redissolved in acetone (1.5 mL) and filtered over non-absorbent cotton wool. The resulting dark orange solution was then cooled in a dry ice bath to give a brown precipitate that was separated by centrifugation (−9° C., 14800 rpm, 5 min, fixed angle rotor) and decantation. The precipitation procedure was repeated three further times and the solid was allowed to dry under vacuum to give PEG reagent 6 (94 mg). Removal of the trimethylsilyl protection group was confirmed by the absence of the methylsilyl signals at 0.2 ppm in the NMR spectrum of the product 6 (DMSO-$d_6$, 400 MHz).

EXAMPLE 3

Hinge Disulfide PEGylation of a Fab Using 20 kDa PEG Reagent 1

To a Fab solution (190 μL, 0.42 mg/mL) in 50 mM Sodium phosphate buffer, pH 7.0, containing 150 mM Sodium Chloride and 10 mM EDTA (ChromPure Human IgG antibody fragment from Jackson ImmunoResearch Laboratories, catalogue number 009-000-007) was added 10 μL of a 100 mM DTT stock solution. After 45 minutes at ambient temperature, the resulting solution was applied to a NAP-5 desalting column (GE healthcare catalogue number 17-0835-01). The flow through was discarded and then 5×400 μL of sodium phosphate buffer, pH 7.0, was added to elute the hinge disulfide reduced Fab. The UV absorbance at 280 nm was measured to determine the protein concentration in each elute fraction. The first fraction contained most of the reduced Fab (0.17 mg/mL, 400 μL).

PEG reagent 1 (20 kDa) was dissolved in water to give a concentration of 2 mg/mL. The PEG solution (18.5 μL, 1.5 molar equivalents to Fab) was added to the first fraction of reduced Fab solution obtained from the NAP-5 column. The resulting solution was incubated at ambient temperature for 12 hours.

The resulting reaction solution was analysed using SDS-PAGE and the resulting gel after staining with InstantBlue protein stain (Novexin) is shown in FIG. 1 along with a sample of reduced and unreduced Fab. Fab is a protein of approximately 50 kDa and on a SDS-PAGE gel runs either as a single band at about 50 kDa when non-reduced or as a band or two bands at around 25 kDa for the reduced form. These are the heavy and light chains which are no longer held together by the hinge disulfide upon reduction and incubation with SDS. The lanes labelled M show the Novex Sharp protein markers (Invitrogen) used as calibrants. The lane labelled 1 shows the Fab before reduction with DTT. The lane labelled 2 shows the DTT reduced Fab and in lane 3 is shown the PEGylation reaction solution. The band present in lane 3 corresponds to hinge disulfide bridged mono-PEGylated Fab product. The lane labelled 4 shows the PEG reagent only (no band visible as PEG does not stain).

EXAMPLE 4

Disulfide PEGylation of Interferon Alpha Using 20 kDa PEG Reagent 1

Figure 2:
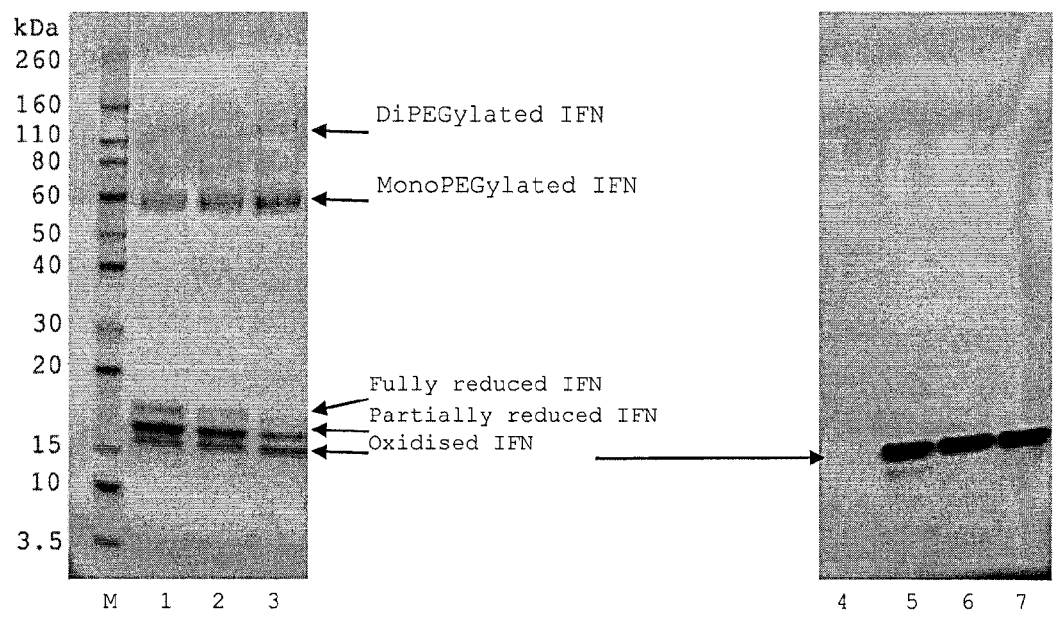
FIG. 2 shows the results of Example 4.

A solution of Interferon α-2b (IFN, 0.5 mg/mL, 1 mL) was prepared in 50 mM sodium phosphate buffer containing 150 mM sodium chloride, 10 mM EDTA and 100 mM Dithiothreitol (DTT), pH 7.3. The solution after incubation for 30 min at ambient temperature was buffer exchanged using a Sephadex G-25 (PD-10, GE healthcare) column to 50 mM sodium phosphate buffer containing 150 mM sodium chloride, 10 mM EDTA, pH 7.3. The resultant reduced IFN solution (0.2 mg/mL, 2 mL) was aliquoted into 100 μL fractions. To the fractions, each containing 0.02 mg of reduced IFN was added 0.5, 1, and 2 molar equivalents of PEG reagent 1 (1.54 μL, 3.08 μL, 6.16 μL respectively of 6.9 mg/mL 20 kDa PEG reagent 1 solution in deionised water). The PEG reagent 1 (0.5, 1, and 2 equivalents) was also incubated with 0.2 mg/mL of native IFN (no reduction) under the same conditions as a control. The solutions were left at ambient temperature for 24 h and the resulting reaction solutions were analysed by SDS-PAGE with the gel stained using InstantBlue (Expedeon) and the results shown in FIG. 2. In FIG. 2, lane 1 shows Novex Sharp Pre-stained protein standards; lane 2 shows Reduced IFN, pH 7.3 incubated with 0.5 eq. PEG reagent 1; lane 3 shows reduced IFN, pH 7.3 incubated with 1 eq. PEG reagent 1; lane 4 shows reduced IFN, pH 7.3 incubated with 2 eq. PEG reagent 1; lane 5 shows control buffer solution with 2 eq. PEG reagent 1; lane 6 shows IFN, pH 7.3 incubated with 0.5 eq. PEG reagent 1; lane 7 shows IFN, pH 7.3 incubated with 1 eq. PEG reagent 1; and lane 8 shows IFN, pH 7.3 incubated with 2 eq. PEG reagent 1

Interferon alpha has two disulfide bonds. In the lanes labelled 2, 3 and 4, which show the PEG reagent 1 conjugation to reduced IFN, bands corresponding to mono-PEGylated and di-PEGylated IFN are visible. Since IFN has only two disulfide bonds, the mono- and di-PEGylation shows that the reduced disulfides are the reactive sites for PEG reagent 1.

This is further confirmed by the results for lanes 5, 6 and 7 where no PEGylation is seen because the IFN disulfides have not been reduced.

EXAMPLE 5

Synthesis of 5 kDa PEG Reagent 6 by Deprotection of the Silyl Protected PEG Compound 5 Using a Basic Resin

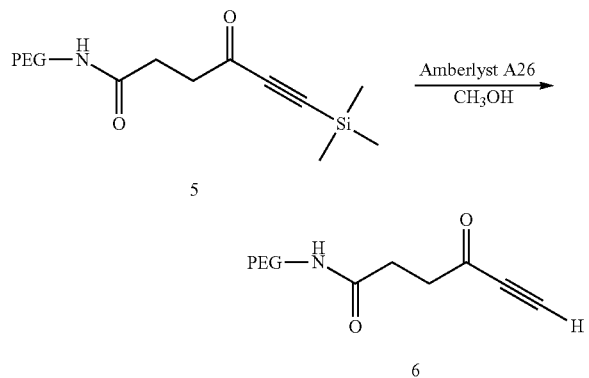

To 5 kDa PEGylated 4-oxo-6-(trimethylsilyl)hex-5-ynoic acid g (0.02 g) and Amberlyst resin-A26 (0.02 g, Acros Organics, cat. No. 202181000) was added methanol (1 mL). The resulting mixture was stirred at room temperature for 3 h. The mixture was then filtered through non-absorbent cotton wool and then volatiles removed from the filtrate using a rotary evaporator. The solid residue remaining was re-dissolved in acetone (10 mL) and the solution then cooled in a −80° C. freezer to yield a light brown precipitate, which was isolated by centrifugation (−9° C., 4000 rpm, 30 min) followed by decantation of the supernatant. The acetone precipitation procedure was repeated 3 times in total and the precipitate was finally dried under vacuum to give the solid product 1 (0.016 g). $^1$H-NMR (400 MHz, CDCl$_3$): δ 2.53 (t, 2H), 2.97 (t, 2H), 3.31 (s, 1H), 3.32-3.82 (br, s, PEG) 6.39 (s, 1H).

EXAMPLE 6

Synthesis of 5 kDa Bis-Sulfide PEG Reagent 8

Step 1. Synthesis of 5-oxo-7,7-bis(p-tolylthio)heptanoic acid 7

A mixture of 5-oxohept-6-ynoic acid 3 (1.0 g), 4-dimethylaminopyridine (DMAP, 0.87 g) and p-toluenethiol (1.77 g) dissolved in dry dichloromethane (15 mL) was stirred at room temperature for 72 h. The reaction mixture was then diluted with ethyl acetate (40 mL) and the resulting organic phase washed with acidified water (2×15 mL, made from adding 2 ml of 1N HCl to 250 ml of deionised water) and finally saturated brine (1×10 mL). Volatiles were removed under reduced pressure (rotary evaporation) to yield a reddish brown 'sticky' residue which was further purified using silica based flash chromatography (Silica gel 100 C$_{18}$-reversed phase, Fluka cat. No. 60754). A mobile phase consisting of hexane:ethyl acetate (60:40 v:v) was used to elute the product 2, (0.32 g, TLC Rf=0.50 using a mobile phase of hexane:ethyl acetate (25:10 v/v) acidified with acetic acid). $^1$H NMR (400 MHz, acetone-d$_6$): δ 1.71 (p, 2H), 2.21 (t, 2H), 2.23 (s, 6H), 2.45 (t, 2H), 2.83 (d, 2H), 4.78 (t, 1H), 7.09 (d, 4H), 7.30 (d, 4H).

Step 2. Conjugation of PEG to Compound 7 to Give PEG Reagent 8

A solution of PEG-amine (0.15 g, 5 kDa, BioVectra cat. No. 0315) in anhydrous toluene (5 mL) was evaporated to dryness under vacuum and then placed under argon. Anhydrous dichloromethane (10 mL) was added to the flask and the resulting solution cooled in an ice-bath. N,N'-diisopropylcarbodiimide (0.012 mL, DIPC) was added under stirring. The reaction mixture was stirred for 18 h, in which time the solution was allowed to warm to room temperature. After 18 hours, volatiles were removed under reduced pressure and the solid residue remaining redissolved in warm acetone (10 mL). Insolubles were then removed by filtration through non-absorbent cotton-wool and the filtrate cooled with a dry-ice bath. The product 8 precipitated as a white precipitate that was separated by centrifugation (−9° C., 4600 rpm, 15 min, swinging bucket rotor) followed by decantation of the liquid phase. The precipitation procedure was repeated three times in total with fresh acetone. The resulting solid was allowed to dry under vacuum to give the product 8 as a white solid (129 mg). $^1$H-NMR (Acetone-$d_6$) δ: 2.18 (t, 2H), 2.34 (s, 6H), 2.45 (t, 2H), 2.82 (d, 2H), 3.38 (s, 3H), 3.30-3.84 (br m, PEG), 4.78 (t, 1H), 6.14 (br s, 1H), 7.12 (d, 4H), 7.36 (d, 4H).

EXAMPLE 7

Synthesis of 5, 10 and 20 kDa PEG Reagent 10 from Propiolic Acid 9

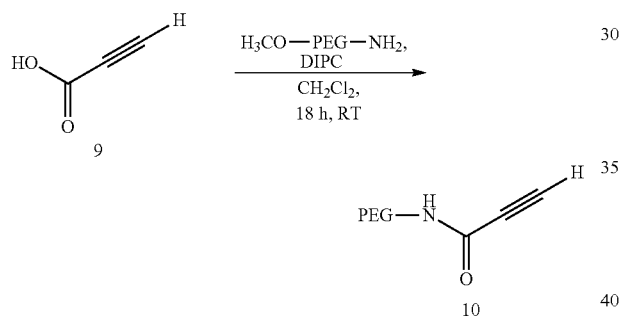

A solution of PEG-amine (0.25 g, 10 kDa, BioVectra cat. No. 6232) in anhydrous toluene (5 mL) was evaporated to dryness under reduced pressure. The dried PEG was then redissolved in anhydrous dichloromethane (10 mL) under argon. To the solution, cooled in an ice bath and under stirring was then added propiolic acid (0.0062 mL) and N,N'-diisopropylcarbodiimide (0.015 mL, DIPC). The reaction mixture was stirred for 18 h, in which time the solution was allowed to warm to room temperature. After 18 h, volatiles were removed under reduced pressure and the solid residue remaining redissolved in warm acetone (10 mL). Insolubles were then removed by filtration through non-absorbent cotton-wool and the filtrate cooled with a dry-ice bath. The product 10 precipitated as a white precipitate that was separated by centrifugation (−9° C., 4000 rpm, 30 min, swinging bucket rotor) followed by decantation of the liquid phase. The precipitation procedure was repeated three times in total with fresh acetone each time. The resulting solid was allowed to dry under vacuum to give the product 9 as a white solid (0.23 mg). $^1$H-NMR (CDCl$_3$) δ: 2.86 (s, 1H), 3.38 (s, 3H), 3.46-4.13 (br m, PEG), 6.79 (s, 1H). The procedure was also performed with 0.25 g of 5 kDa and 20 kDa PEG (0.012 mL and 0.003 mL of propiolic acid respectively) to afford 0.22 g and 0.25 g of product 5 kDa and 20 kDa PEG reagent 10 respectively.

EXAMPLE 8

Thiol PEGylation of Interferon Alpha Using 10 kDa PEG Reagent 6

To a solution of interferon alpha (IFN, 0.36 mg/mL, 1 mL) was prepared in 50 mM sodium phosphate buffer containing 150 mM sodium chloride, 10 mM EDTA, pH 7.3 was added to DTT (10 mM final concentration). After 30 min at ambient temperature, the reaction solution was buffer exchanged using a Sephadex G-25 column (PD-10, GE healthcare) to 50 mM sodium phosphate containing 150 mM sodium chloride and 10 mM EDTA, pH 7.3 to give 2 ml of a reduced IFN solution (0.15 mg/ml). To the reduced IFN (0.015 mg, 100 μL) was added 10 kDa PEG reagent 6 (0.74 μl of a 5 mg/mL solution in deionised water). The PEG reagent 6 was also incubated with 0.15 mg/mL of non-reduced IFN under the same conditions as a control for reduced disulfide PEGylation. The solutions were incubated at 20° C. for 16 h and then analysed by SDS-PAGE with the gels stained using InstantBlue (Expedeon Ltd) and the results are shown in FIG. 3.

Figure 3:
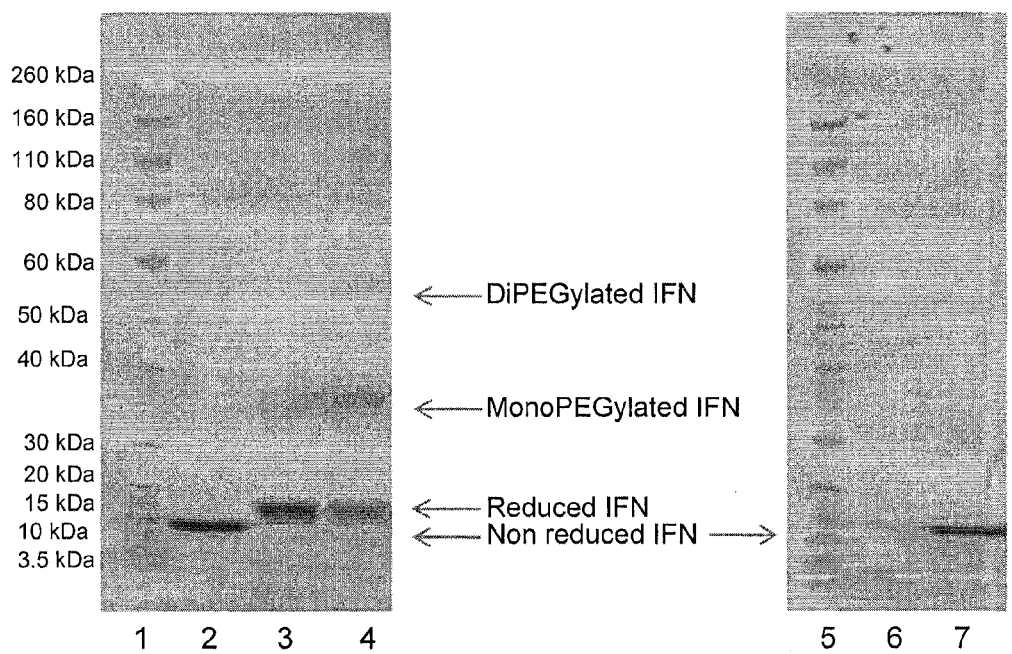
FIG. 3 shows the results of Example 8.

In FIG. 3, lanes 1 and 5 show NOVEX® Sharp Protein Standards (Invitrogen); lane 2 shows the starting IFN before PEGylation; line 3 shows IFN reduced with 10 mM DTT; lane 4 shows reduced IFN incubated with PEG reagent 6; lane 6 shows PEG reagent 6; lane 7 shows non-reduced IFN incubated with PEG reagent 6. In the lane labelled 4, successful PEGylation using PEG reagent 6 of the two disulfide containing protein IFN alpha is seen with bands corresponding to mono-PEGylated (bands around 35 kDa) and di-PEGylated IFN (55 kDa) clearly visible. There was no PEGylation visible when the protein was not first reduced (lane 7).

EXAMPLE 9

Thiol PEGylation of Interferon Alpha Using 5 kDa, 10 kDa and 20 kDa PEG Reagent 10

Figure 4:
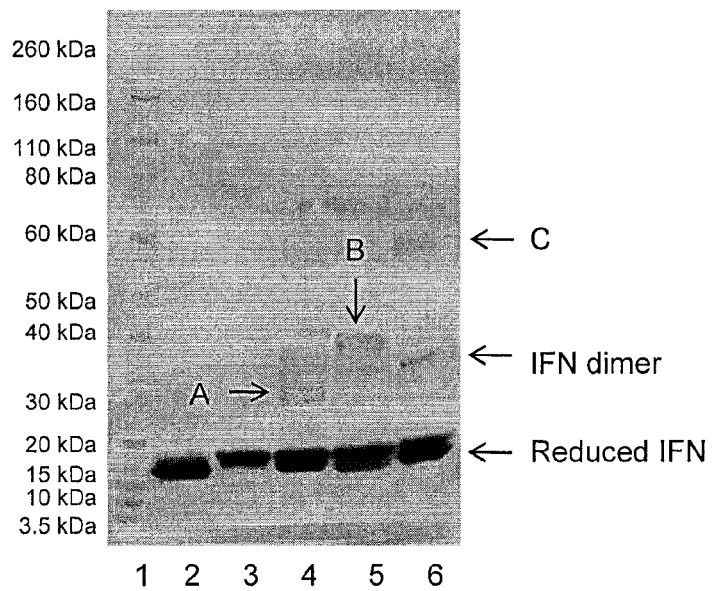
FIG. 4 shows the results of Example 9.

A solution of interferon alpha (IFN, 0.5 mg/mL, 1 mL) in 50 mM sodium phosphate buffer containing 150 mM sodium chloride, 10 mM EDTA at pH 7.3 was added DTT (10 mM). After 30 min at ambient temperature, the reaction solution was buffer exchanged using a Sephadex G-25 column (PD-10, GE Healthcare) to 50 mM sodium phosphate containing 150 mM sodium chloride and 10 mM EDTA, pH 7.3 to give a 2 ml of a reduced IFN solution (0.24 mg/ml). To separate 100 μL aliquots (0.024 mg) of the reduced protein, was added 2 molar equivalents of varying size PEG reagent 10 (4.8 μl respectively of 2.5 mg/mL 5 kDa PEG reagent 10 solution, 5 mg/mL 10 kDa PEG reagent 10 solution and 10 mg/mL 20 kDa PEG reagent 10 solution; each solution of reagent 9 was prepared in deionised water). The resulting solutions were incubated at 20° C. for 16 h and then analysed by SDS-PAGE with protein staining using InstantBlue (Expedeon Ltd). The results are shown in FIG. 4. In FIG. 4, lane 1 shows NOVEX® Sharp Protein Standards; lane 2 shows the starting non-reduced IFN; lane 3 shows IFN after reduction with 10 mM DTT; lane 4 shows reduced IFN, incubated with 5 kDa PEG reagent 10; lane 5 shows reduced IFN incubated with 10 kDa PEG reagent 1; lane 6 shows reduced IFN incubated with 20 kDa PEG reagent 10.

In the lanes labelled 4, 5, 6, which show respectively the conjugation of 5 kDa, 10 kDa, 20 kDa PEG reagent 10 with reduced IFN, successful PEGylation is observed with the bands (labelled as A, B, C) corresponding to mono-PEGylated IFN.

Figure 5:
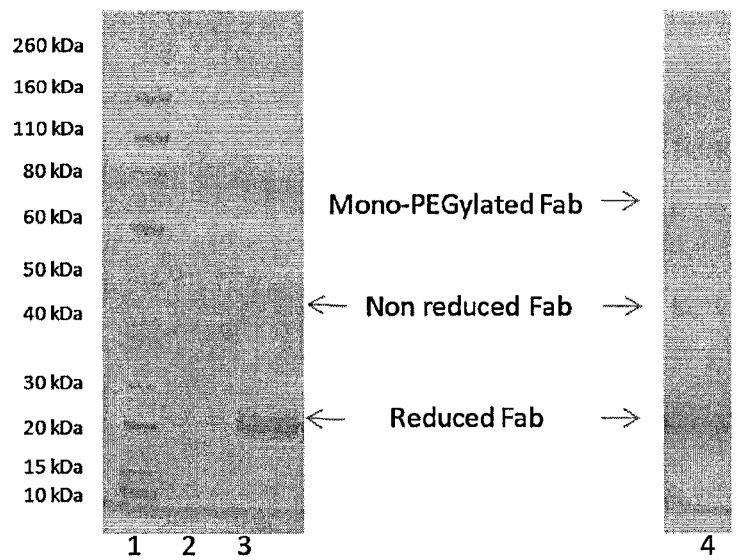
FIG. 5 shows the results of Example 10.

Example 10. Thiol PEGylation of a Fab using 10 kDa PEG reagent 6 To a Fab solution (85 µl; 1.3 mg/mL; in 0.01M sodium phosphate buffer containing 0.25 M sodium chloride, pH 7.6; AffiniPure Goat Anti-Rat IgG antibody Fab fragment from Jackson ImmunoResearch Laboratories, cat. No. 112-007-003) was added deionised water (115 µL) and 100 mM of a DTT solution in water (50 µL). The solution after incubation for 45 min at ambient temperature was buffer exchanged using a NAP-5 desalting column (GE healthcare, cat. No. 17-0835-01) into a solution 50 mM sodium phosphate, 150 mM NaCl, 10 mM EDTA, pH 8.0 to give a reduced Fab fragment solution (0.140 mg/mL; 0.7 mL). To a 45 µl aliquot of the reduced Fab (6.3 µg) was added PEG reagent 6 (0.64 µL of a 5 mg/mL solution of 10 kDa PEG reagent 6 solution prepared in deionised water, 2.5 molar equivalents to Fab). The solution was incubated at 20° C. for 16 h and the analysed by SDS-PAGE with the gel stained using InstantBlue (Expedeon Ltd). The result is shown in FIG. 5. In FIG. 5, lane 1 shows NOVEX® Sharp Protein Standards; lane 2 shows non reduced Fab as a band at about 50 kDa; line 3 shows reduced Fab with 20 mM DTT as a band at about 25 kDa; line 4 shows reduced Fab when allowed to react with 10 kDa PEG reagent 6.

EXAMPLE 11

Synthesis of 10 kDa PEG Reagent 11

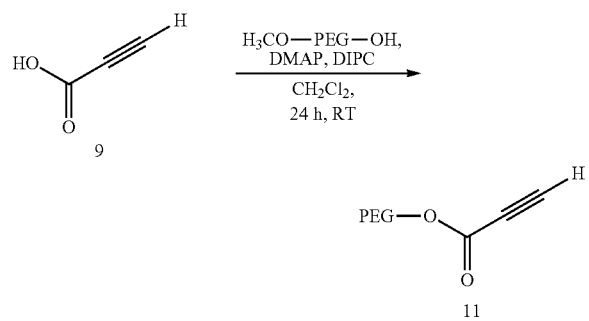

A solution of methoxy-PEG-OH (0.05 g, IrisBiotech GmbH, Cat no. PEG 1033), propiolic acid (0.006 mL) and 4-dimethylaminopyridine (0.0006 g, DMAP) in anhydrous toluene (3 mL) was evaporated to dryness under reduced pressure. The dried mixture was then redissolved in anhydrous dichloromethane (5 mL) under argon. To the solution, while stirring in an ice bath was added N,N'-diisopropylcarbodiimide (0.0016 mL, DIPC). The reaction mixture was stirred for 24 h, in which time the solution was allowed to warm to room temperature. After 24 h, the volatiles were removed under reduced pressure (rotary evaporation) and the resulting reddish-brown solid was further dried in vacuum for 0.5 h. The solid was redissolved in acetone and filtered through non-absorbent cotton wool to remove insolubles and the filtrate was cooled in a dry-ice bath. The product 11 precipitated as a reddish-brown solid that was separated by centrifugation (−9° C., 4000 rpm, 30 min, swinging bucket rotor) and the resulting liquid phase was decanted. The acetone precipitation procedure was repeated 3 times in total with fresh acetone. The resulting solid was allowed to dry under vacuum to give the product 11 as reddish-brown solid (0.048 g). $^1$H-NMR (CDCl$_3$) δ: 3.01 (s, 1H), 3.38 (s, 3H), 3.45-4.83 (br, s, PEG).

EXAMPLE 12

Thiol PEGylation of Interferon Alpha Using 10 kDa PEG Reagent 11

A solution of interferon alpha (IFN, 0.93 mg/mL, 1 mL) was prepared in 50 mM sodium phosphate buffer containing 150 mM sodium chloride, 10 mM EDTA and 10 mM DTT, pH 7.3. The solution after incubation for 30 min at ambient temperature was buffer exchanged using a PD-10 column (GE Healthcare) to a 50 mM sodium phosphate buffer containing 150 mM sodium chloride and 10 mM EDTA, pH 7.3.

The resultant reduced IFN solution (0.49 mg/mL, 2 mL) was aliquoted into 50 µL fractions. To three separate 50 µL aliquots of the reduced protein was added 0.5, 1 and 2 molar equivalents of PEG reagent 11 (1.2 µL, 2.5 µL, 4.9 µL of a 5 mg/mL 10 kDa PEG reagent 11 solution prepared in deionised water respectively). The resulting solutions were incubated at 20° C. for 16 h. The PEG reagent 11 (0.5, 1 and 2 equivalents) was also incubated with non-reduced IFN under the same conditions. The resulting reaction solutions were analysed by SDS-PAGE with the gel stained using InstantBlue (Expedeon Ltd) and the results are shown in FIG. 6.

Figure 6:
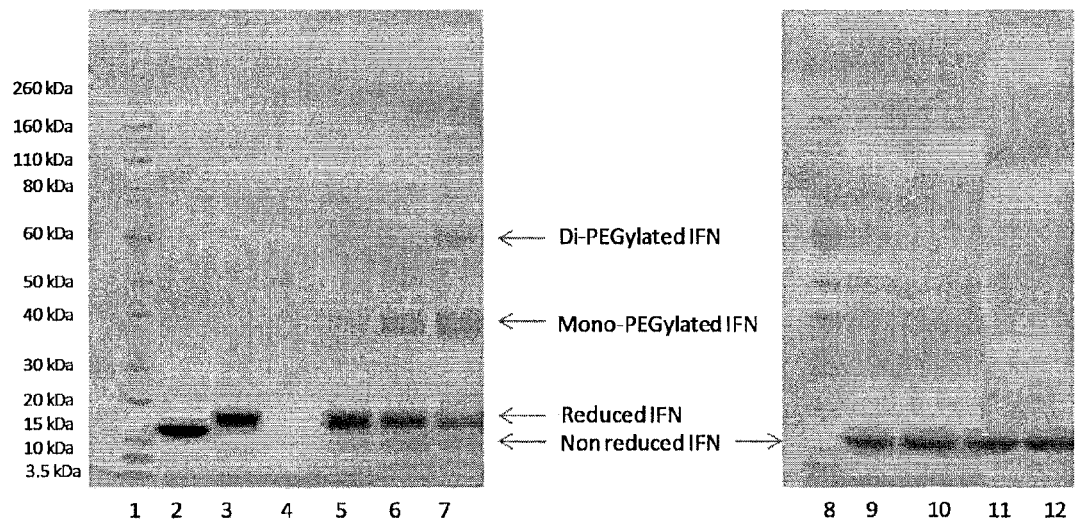
FIG. 6 shows the results of Example 12.

In FIG. 6, lane 1 shows NOVEX® Sharp Protein Standards; lane 2 shows non reduced IFN; lane 3 shows IFN reduced with 10 mM DTT; lane 4 shows PEG reagent 11 which did not stain; lane 5 shows reduced IFN incubated with 0.5 eq. 10 kDa PEG reagent 11; lane 6 shows reduced IFN incubated with 1 eq. 10 kDa PEG reagent 11; lane 7 shows reduced IFN incubated with 2 eq. 10 kDa PEG reagent 11; lane 8 shows NOVEX® Sharp Protein Standard; lane 9 shows non reduced IFN; lane 10 shows non-reduced IFN incubated with 0.5 eq. 10 kDa PEG reagent 11: lane 11 shows non-reduced IFN incubated with 1 eq. 10 kDa PEG reagent 11; lane 12 shows non-reduced IFN incubated with 2 eq. 10 kDa PEG reagent 11: In lanes 5, 6 & 7 there are strong bands visible corresponding to mono- and di-PEGylated IFN. When non-reduced IFN was incubated with PEG reagent 11, the strongly stained bands of PEGylated IFN are not visible (lanes 10, 11, 12).

EXAMPLE 13

Thiol PEGylation of a Fab Using 10 kDa PEG Reagent 11

To a solution of Fab (85 µL; 1.3 mg/mL; in 0.01 M sodium phosphate buffer containing 0.250 M sodium chloride, pH 7.6; AffiniPure Goat Anti-Rat IgG antibody Fab fragment from Jackson ImmunoResearch Laboratories, catalogue number 112-007-003) was added 115 µL of deionised water and 50 µL of a 100 mM DTT stock solution prepared in deionised water. The resulting solution after incubation for 45 min at ambient temperature was buffer exchanged into 50 mM sodium phosphate buffer, containing 150 mM sodium chloride and 10 mM EDTA, pH 8.0, using a NAP-5 desalting column (GE healthcare, catalogue number 17-0835-01). The resultant reduced Fab fragment solution (0.13 mg/mL; 0.7 mL) was aliquoted into 70 μL fractions. To separate aliquots of the reduced Fab (9.0 μg) was added respectively 5 and 10 molar equivalents of PEG reagent 11 (1.9 μL, 3.8 μL respectively of a 5 mg/mL 10 kDa PEG reagent 11 solution prepared in deionised water). The solutions were incubated at 20° C. for 16 h and the resulting reaction solutions then analysed by SDS-PAGE with the gel stained using InstantBlue (Expedeon) and the results are shown in FIG. 7.

Figure 7:
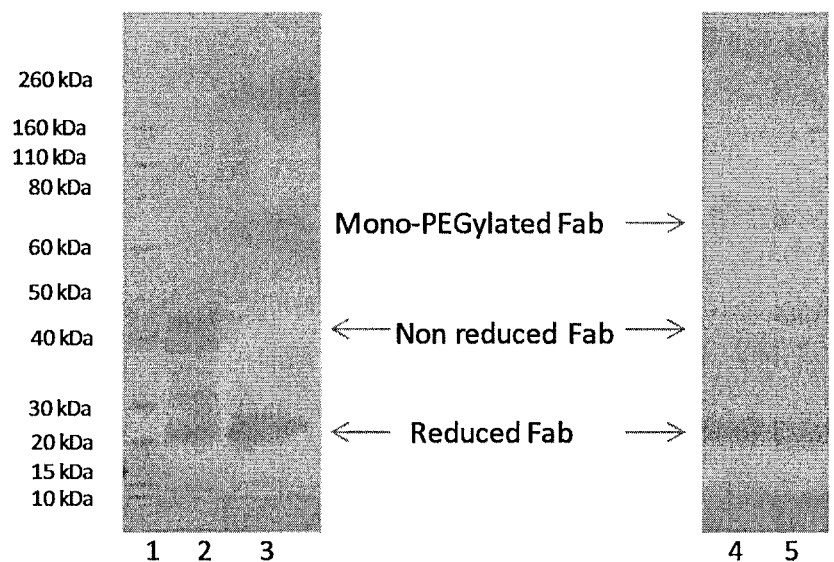
FIG. 7 shows the results of Example 13.

In FIG. 7, lane 1 shows NOVEX® Sharp Protein Standards; lane 2 shows non reduced Fab; lane 3 shows reduced Fab; lane 4 shows reduced Fab incubated with 5 eq. of 10 kDa PEG reagent 11; lane 5 shows reduced Fab incubated with 10 eq. of 10 kDa PEG reagent 11. In lanes 4 and 5, a band is visible that corresponds to mono-PEGylated Fab, labelled in FIG. 7.

EXAMPLE 14

Synthesis of PEG Reagents 12 and 13

Step 1. Synthesis of 10 kDa PEG Bis-Sulfide 12

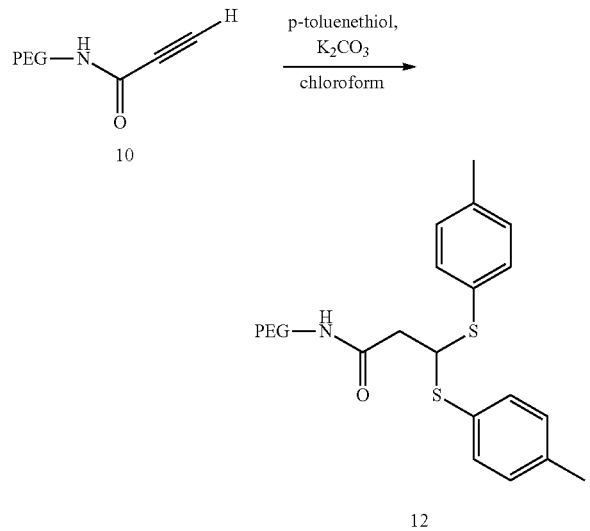

To 10 kDa PEG reagent 10 (0.02 g), p-toluenethiol (0.002 g) and potassium carbonate (0.08 g) was added chloroform (1 mL) and the resulting mixture was stirred at room temperature for 18 h. After 18 h, volatiles were removed by rotary evaporation and the white solid residue remaining was allowed to redissolve in warm acetone (6 mL). Insolubles were removed by filteration through non-absorbent cotton wool. The filtrate was then cooled with dry ice to precipitate a white solid which was isolated by centrifugation (−9° C., 4000 rpm, 30 min, swinging bucket rotor) followed by decantation of the liquid phase. The precipitation procedure was repeated 3 times in total with fresh acetone each time. The final precipitate was then allowed to dry in vacuo to give product 12 as a white solid (0.019 g). $^1$H-NMR (CDCl$_3$) δ: 2.35 (s, 6H), 3.38 (s, 3H), 3.46-4.82 (br, s, PEG), 7.15 (d, 4H), 7.38 (d, 4H).

Step 2. Oxidation of PEG Compound 12 to Sulfone PEG Reagent 1

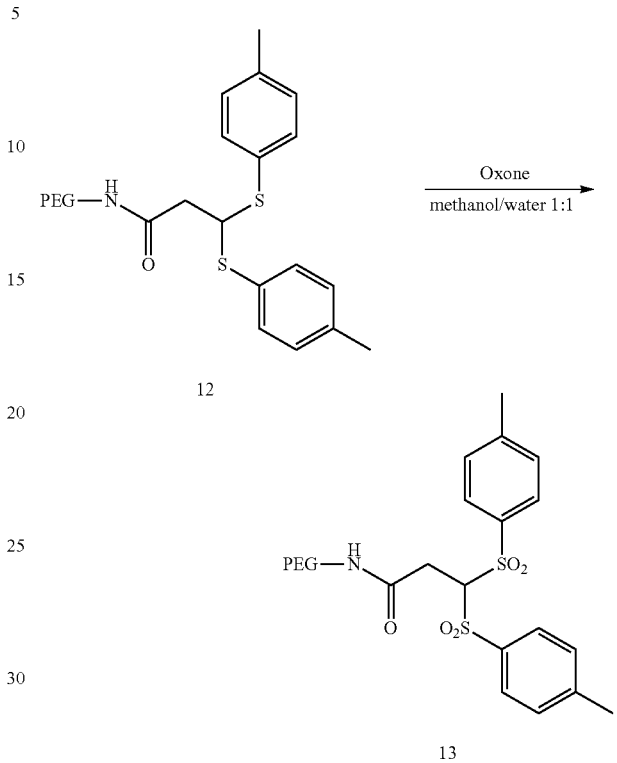

To compound 11 (0.01 g) and Oxone (0.02 g, Sigma Aldrich, cat. No. 22,803-6) was added methanol (0.5 mL) and water (0.5 mL). The resulting mixture was allowed to stir at room temperature for 18 h. After 18 h, volatiles were removed under reduced pressure (rotary evaporation) and the solid residue allowed to further dry in a vacuum oven for 0.5 h. The resulting white solid was allowed to redissolve in acetone (3.0 mL) and insolubles were removed by filtration through non-absorbent cotton wool. The filtrate was then cooled with dry ice to precipitate a white solid which was isolated by centrifugation (−9° C., 4000 rpm, 30 min, swinging bucket rotor) followed by decantation of the liquid phase. The precipitation procedure was repeated 3 times in total with fresh acetone each time. The final precipitate was then allowed to dry in vacuo to give PEG reagent 13 as a white solid (0.006 g). $^1$H-NMR (CDCl$_3$) δ: 2.44 (s, 6H), 3.38 (s, 3H), 3.45-4.83 (br, s, PEG), 7.35 (d, 4H), 7.88 (d, 4H).

EXAMPLE 15

Thiol PEGylation of Interferon Alpha Using 10 kDa PEG Reagent 130

Figure 8:
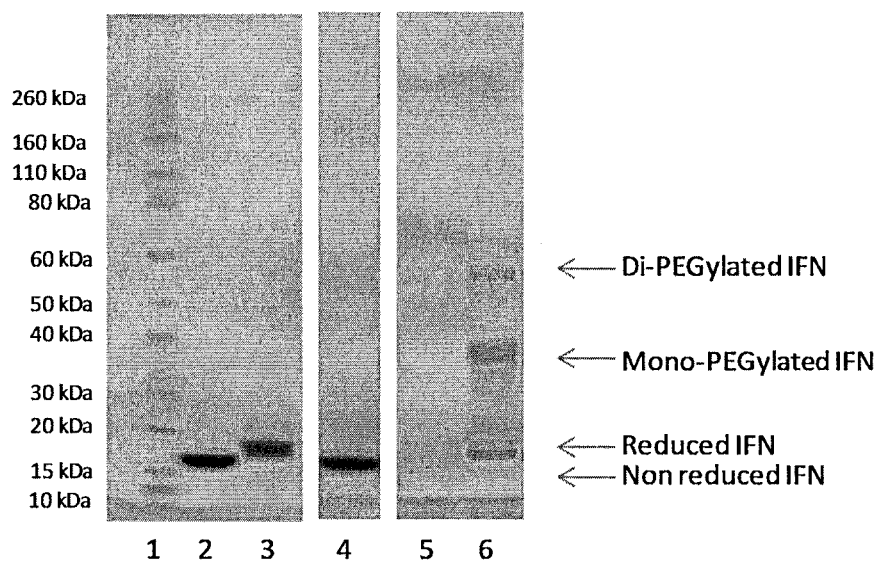
FIG. 8 shows the results of Example 15.

A solution of interferon alpha (IFN, 0.93 mg/mL, 1 mL) was prepared in 50 mM sodium phosphate buffer containing 150 mM sodium chloride, 10 mM EDTA and 10 mM DTT, pH 7.3. The solution after incubation for 30 min at ambient temperature was buffer exchanged using a PD-10 column (GE Healthcare) to 50 mM sodium phosphate buffer containing 150 mM sodium chloride and 10 mM EDTA pH 7.3 (0.49 mg/mL reduced IFN, 2 mL). To a 50 μL aliquot of the reduced IFN (24 μg) was added 0.5 molar equivalents of PEG reagent 13 (1.2 μL of a 5 mg/mL solution of 10 kDa PEG reagent 13 prepared in deionised water). The solution was incubated at 20° C. for 16 h and then analysed by SDS-PAGE with the gel stained using InstantBlue (Expedeon Ltd). A repeat reaction was also performed with non-reduced IFN. The results are shown in FIG. 8. In FIG. 8, lane 1 shows NOVEX® Sharp Protein Standards; lane 2 shows non-reduced IFN, lane 3 shows IFN reduced with 10 mM DTT; lane 4 shows non reduced IFN incubated with 0.5 eq. 10 kDa PEG reagent 13; lane 5 shows PEG reagent 13 which did not stain; lane 6 shows reduced IFN incubated with 0.5 eq. of 10 kDa PEG reagent 13 Two strong additional bands are seen in lane 6 corresponding to mono- and di-PEGylated IFN which are not visible in when the protein is not first reduced (lane 4).

EXAMPLE 16

Thiol PEGylation of a Fab Using 10 kDa PEG Reagent 13

To a Fab solution (85 μL; 1.3 mg/mL; in 0.01M sodium phosphate buffer containing 0.25 M sodium chloride, pH 7.6; AffiniPure Goat Anti-Rat IgG antibody Fab fragment from Jackson ImmunoResearch Laboratories, catalogue number 112-007-003) was added deionised water (115 μL) and an aqueous 100 mM DTT stock solution (50 μL). After 45 min at ambient temperature, the solution was buffer exchanged into 50 mM sodium phosphate buffer containing 150 mM sodium chloride and 10 mM EDTA, pH 8.0 using a NAP-5 desalting column (GE healthcare, catalogue number 17-0835-01). The resultant reduced Fab solution (0.13 mg/mL; 0.7 mL) was aliquoted into 70 μL fractions. To three separate 70 μL fractions (each containing 9.0 μg of reduced Fab) was added 1.5, 2.5 and 5 molar equivalents of PEG reagent 13 respectively (0.56 μL, 0.95 μL and 1.9 μL respectively of a 5 mg/mL solution of 10 kDa PEG reagent 13 previously incubated at 37° C. in 5 mM sodium phosphate buffer containing 2 mM EDTA and 15 mM sodium chloride, pH 8.0 for 8 h). The solutions were incubated at 20° C. for 16 h and then analysed by SDS-PAGE with the gel stained using InstantBlue (Expedeon Ltd). The results are shown in FIG. 9.

Figure 9:
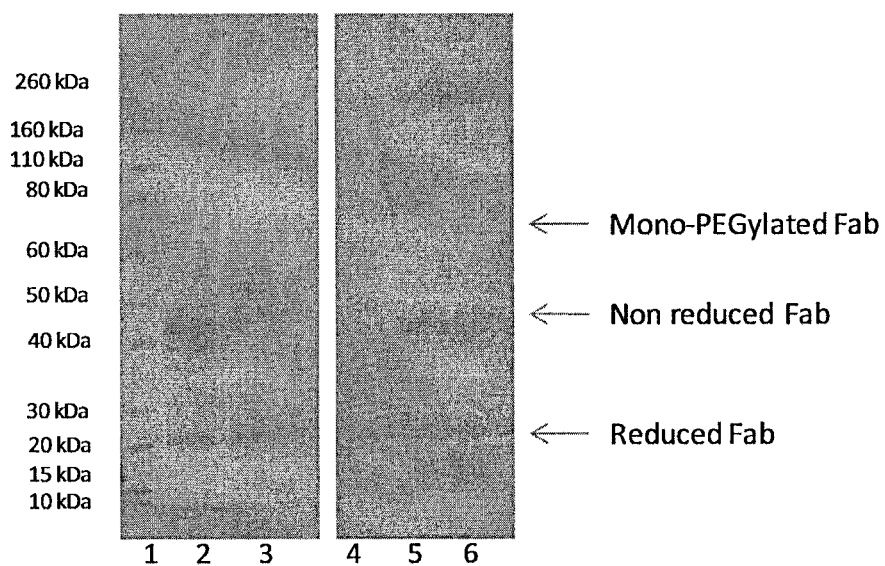
FIG. 9 shows the results of Example 16.

In FIG. 9, lane 1 shows NOVEX® Sharp Protein Standards; lane 2 shows non reduced Fab; lane 3 shows reduced Fab; lane 4 shows reduced Fab incubated with 1.5 eq. of 10 kDa PEG reagent 13; lane 5 shows reduced Fab incubated with 2.5 eq. of 10 kDa PEG reagent 13; lane 6 shows reduced Fab incubated with 5 eq. of 10 kDa PEG reagent 13. A band is clearly visible in lanes 4, 5 and 6 corresponding to mono-PEGylated Fab.

The invention claimed is:

1. A process for the preparation of a compound of the general formula:

$$X-Q-W-CHR^1-CR^2\begin{matrix}Z^1\\ \diagdown\\ Z^2\end{matrix} \quad (I)$$

in which X represents a polymer,
Q represents a linking group;
W represents an electron-withdrawing moiety or a moiety preparable by reduction of an electron-withdrawing moiety;
each of $R^1$ and $R^2$ independently represents a hydrogen atom or a $C_{1-4}$alkyl group; and either $Z^1$ represents a protein or a peptide linked to $CR^2$ via a nucleophilic moiety, and $Z^2$ represents a molecule linked to $CR^2$ via a nucleophilic moiety, or $Z^1$ and $Z^2$ together represent a single group derived from a protein or peptide linked to $CR^2$ via two nucleophilic moieties;

which comprises reacting a compound of the general formula:

$$X-Q-W'-CR^1R^{1'}-CR^2.L.L' \quad (II)$$

in which X and Q have the meanings given for the general formula I;
W' represents an electron-withdrawing moiety;
either $R^1$ represents a hydrogen atom or a $C_{1-4}$alkyl group, $R^{1'}$ represents a hydrogen atom, and each of L and L' independently represents a leaving group; or
$R^1$ represents a hydrogen atom or a $C_{1-4}$alkyl group, L represents a leaving group, and $R^{1'}$ and L' together represent a bond; or
$R^1$ and L together represent a bond and $R^{1'}$ and L' together represent a bond; and
$R^2$ represents a hydrogen atom or a $C_{1-4}$ alkyl group;
with a protein or a peptide containing at least one nucleophilic group, and optionally subsequently with a second molecule containing a nucleophilic group;
and if desired, converting the resulting compound of the general formula I in which W represents an electron-withdrawing moiety into a corresponding compound in which W represents a moiety preparable by reduction of an electron-withdrawing moiety.

2. A process as claimed in claim 1, in which X is a polyalkylene glycol, a polyvinylpyrrolidone, a polyacrylate, a polymethacrylate, a polyoxazoline, a polyvinylalcohol, a polyacrylamide or polymethacrylamide, a HPMA copolymer, a polyester, polyacetal, poly(ortho ester), polycarbonate, poly(imino carbonate), a polyamide, a copolymer derived from two or more alkylene oxides or from an alkylene oxide and a polyester, polyacetal, poly(ortho ester), or a poly(amino acid), a copolymer of divinylether-maleic anhydride and styrene-maleic anhydride, a polysaccharide, polyglutamic acid, or a copolymer of a saccharides or an amino acid with an alkylene oxide or methacrylic acid.

3. A process as claimed in claim 1, in which X is a water-soluble synthetic polymer.

4. A process as claimed in claim 3, in which X is a polyethylene glycol.
direct bond, an alkylene group, or an optionally-substituted aryl or heteroaryl group, any of which may be terminated or interrupted by one or more oxygen atoms, sulphur atoms, —NR groups (in which R represents a hydrogen atom or an alkyl or aryl group), keto groups, —O—CO— groups and/or —CO—O— groups.

5. A process as claimed in claim 1, in which Q represents a direct bond, an alkylene group, or an optionally-substituted aryl or heteroaryl group, any of which may be terminated or interrupted by one or more oxygen atoms, sulphur atoms, —NR groups (in which R represents a hydrogen atom or an alkyl or aryl group), keto groups, —O—CO— groups, and/or —CO—O— groups.

6. A process as claimed in claim 1, in which W represents a keto group CO, an ester group —O—CO—, an amide group —NH—CO—, or a sulphone group —$SO_2$—, or a group obtained by reduction of such a group.

7. A process as claimed in claim 1, in which $Z^1$ and $Z^2$ together represent a single group derived from a protein.

8. A process as claimed in claim 7, in which $Z^1$ and $Z^2$ together form a single group derived from a protein which is linked to $CR^2$ via two thiol groups which have been derived from a disulfide bridge in the protein.

9. A process as claimed in claim 7, in which $Z^1$ and $Z^2$ together form a single group derived from a protein which is linked to $CR^2$ via two histidine residues.

10. A process as claimed in claim 9, in which said two histidine residues form part of a polyhistidine tag.

11. A process as claimed in claim 1, in which a leaving group L or L' represents —SR, —SO$_2$R, —OSO$_2$R, —NR$_3$, —N$^+$HR, —N$^+$H$_2$R, halogen, or —OØ, in which R represents a hydrogen atom or an alkyl or an aryl group, and Ø represents a substituted aryl group containing at least one electron-withdrawing substituent.

12. A process as claimed in claim 1, in which W' represents a keto group, an ester group, an amide group, or a sulfone group.

* * * * *